United States Patent [19]
Guern et al.

[11] Patent Number: 5,107,845
[45] Date of Patent: Apr. 28, 1992

[54] METHOD AND DEVICE FOR MONITORING HUMAN RESPIRATION

[75] Inventors: Yves F. C. Guern, Pourrières; Jean-Luc M. Weber, Salon de Provence; Marc R. Tommasi, Marseille, all of France

[73] Assignee: Bertin & Cie, Cedex, France

[21] Appl. No.: 460,133

[22] PCT Filed: Nov. 23, 1988

[86] PCT No.: PCT/FR88/00570

§ 371 Date: May 23, 1990

§ 102(e) Date: May 23, 1990

[87] PCT Pub. No.: WO89/04633

PCT Pub. Date: Jun. 1, 1989

[51] Int. Cl.$^5$ .............................................. A61B 5/08
[52] U.S. Cl. ...................................... 128/664; 128/721
[58] Field of Search ................. 340/573; 128/721, 664

[56] References Cited

U.S. PATENT DOCUMENTS

| | | | |
|---|---|---|---|
| 3,796,208 | 3/1974 | Bloice | 128/721 |
| 3,875,929 | 4/1975 | Grant | 128/721 |
| 4,122,427 | 10/1978 | Karsh | 128/721 |
| 4,350,166 | 9/1982 | Mobarry | 128/664 |
| 4,913,150 | 4/1990 | Cheung | 128/633 |

FOREIGN PATENT DOCUMENTS

| | | | |
|---|---|---|---|
| 3109026 | 9/1982 | Fed. Rep. of Germany | 128/721 |
| 2141047 | 1/1973 | France | |

OTHER PUBLICATIONS

H. Teichtahl et al., "Measurement of Vitro Ciliary Beat Frequency: A Television-Video Modification of the Transmitted Light Technique" in Medical & Biological Engineering & Computing, vol. 24, No. 2, Mar. 1986, pp. 193-196.

Thomas Uter, "A Real-Time Video System . . . Two Objects" in IEEE Transactions on Biomedical Engineering, vol. 24, No. 1, Jan. 1977, pp. 75-78.

V. Macellari et al., "Comparison Among Remote Sensing Systems for Human Movement Measurement," in Proceedings of Melecon '85, Madrid, vol. 1, Oct. 1985, pp. 71-75.

Primary Examiner—Kyle L. Howell
Assistant Examiner—Robert L. Nasser, Jr.
Attorney, Agent, or Firm—Watson, Cole, Grindle & Watson

[57] ABSTRACT

A method for monitoring respiration by illuminating the body of the subject with a luminous flux, where a lens is used to form on a set of photosensitive elements, an image of at least one region of the space within which a person under surveillance is capable of moving, a light source is used for illuminating the area, fine control and readout circuits are connected to the photosensitive elements, an analog to digital converter is to the control circuit, and a microprocessor is used to compare successive signals from the photosensitive elements and which is used to determine any significant variations in the successive signals which are due to respiration of the person being monitored. An alarm is also included which is triggered in response to an absence of variations on successive signals.

18 Claims, 2 Drawing Sheets

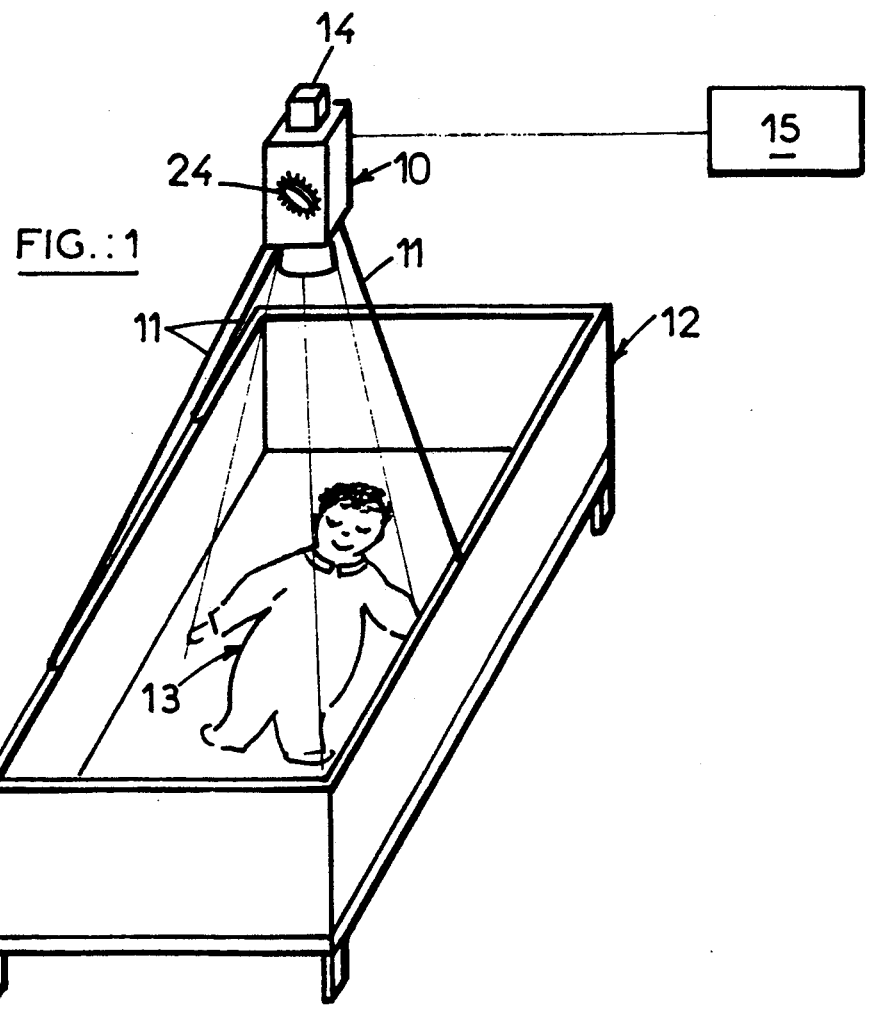
FIG.:1
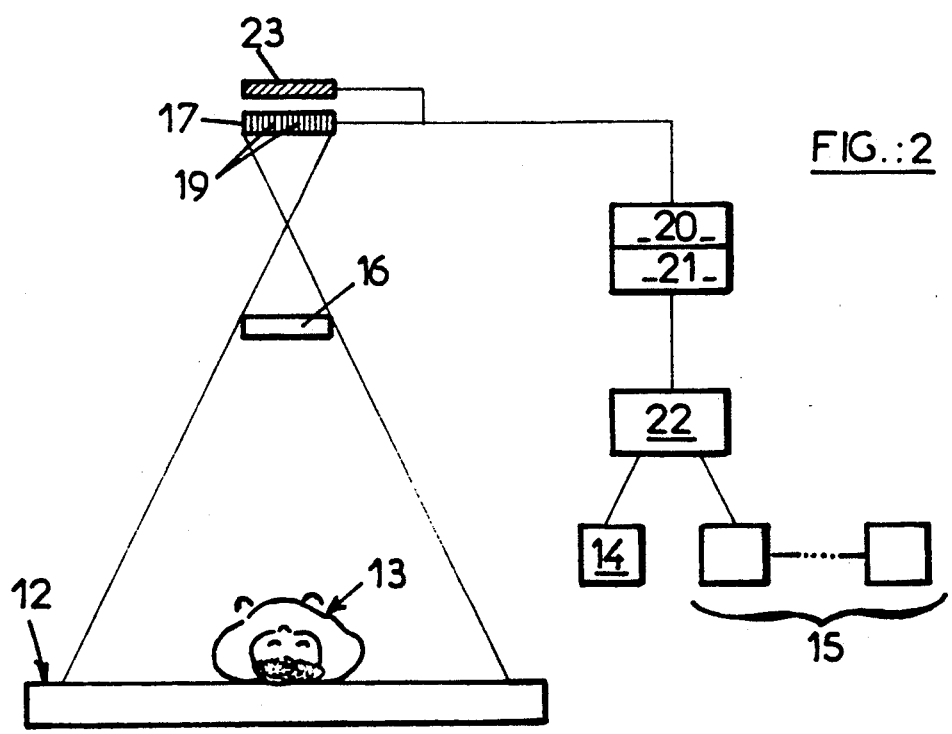
FIG.:2

FIG.:3
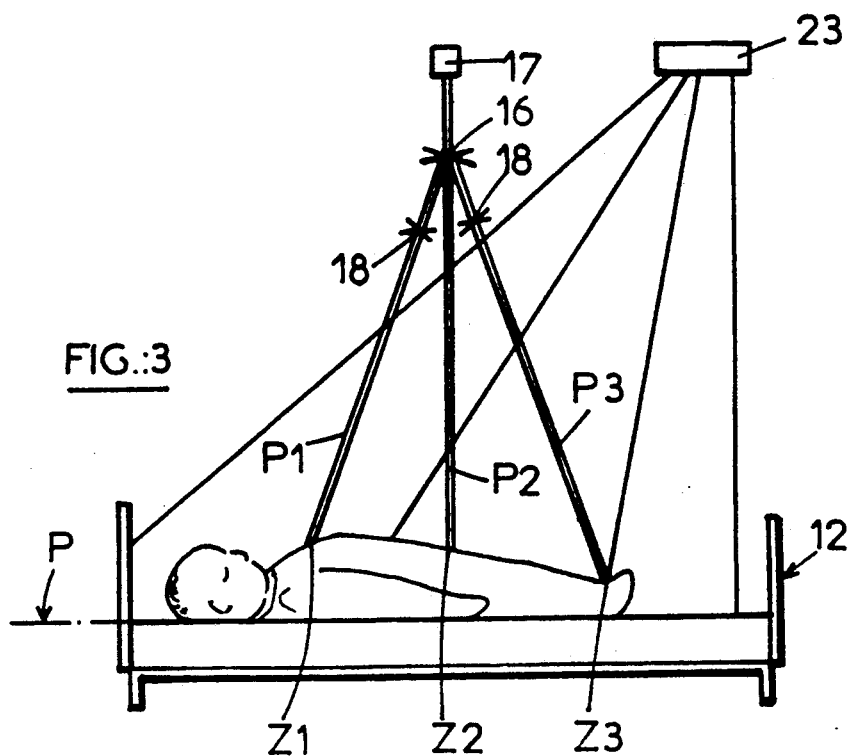
FIG.:4A  FIG.:4B
a
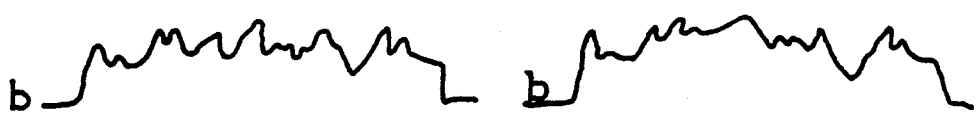
b
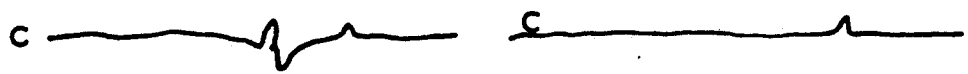
c
d
e  24  25  e  25
f  24  f

METHOD AND DEVICE FOR MONITORING HUMAN RESPIRATION

BACKGROUND OF THE INVENTION

The invention relates to a method and a device for monitoring the respiration of an individual, especially with a view to detecting a respiratory insufficiency, apnoea or dyspnoea, during the sleep of a baby or of a bedridden patient.

Many cases have been recorded of sudden death of babies or young infants aged from one week to two years due to a dysfunction of the respiratory automatisms. In approximately 75% of these cases of respiratory arrest there are no warning signs.

Early detection of these events thus requires permanent monitoring of the regularity of the respiration of the infants. For this purpose various apparatuses have been proposed, which can be classified in two categories.

A first type of detection apparatus requires a direct contact with the subject. These apparatuses use a displacement transducer which records the variations in the thoracic expansion (extensometer gauge, Hall effect sensor, etc.) or the modification in the distribution of the pressures under the mattress supporting the neonate (capacitive, resistive or inductive effect sensors, or sensors for measuring local pressure). The first are not particularly convenient to use and are the cause of accidents as a result of the permanent connection which there must be between the sleeping infant and the detection apparatus, while the second are expensive, because of the necessary attachment of the network of sensors to the bed of the infant, and are of questionable reliability even when recourse is made to sensors of very great sensitivity.

Since the apparatuses of the second type do not necessitate direct contact with the subject, they have the advantage of not interfering with the movements of the latter during his or her sleep. These apparatuses can be based on the detection of the expiratory breathing (thermistor, infrared photodetector, etc.), but they can then be caused to fail in the event of significant movements of the subject (anterior-posterior or lateral turning). Other apparatuses make use of ultrasonic, infrared or other volumetric sensors: these sensors are well suited when the scene is relatively static, that is to say, when the only movement of the individual is due to his or her breathing, but the information which they supply is more difficult to make use of when the subject moves within the field of observation.

Among the apparatuses for detection without contact there is also known, from French Patent No. 2,141,047; a monitoring apparatus by means of which the body of the individual is subjected to microwave radiation.

As the individual breathes, the frequency of the reflected radiation is different at each instant from that of the incident radiation because of the movement of the wall of the thoracic cage, and the difference in frequency between the waves emitted and the waves received is converted into a signal representing the current rate of movement of the thoracic wall at each instant of the respiratory cycle.

If the level of this signal falls below a certain threshold, and if this situation continues beyond a predetermined period of time, an alarm is triggered, signalling respiratory arrest.

The apparatus therefore comprises a source of microwave radiation which is active, directive and radiates in a very narrow frequency range.

Recourse to the microwave technique requires equipment (aerials, electrical feed circuits and electronic processing circuits) which are relatively expensive and consume large amounts of electrical energy.

The use thereof is tricky and requires certain precautions to be taken so that the results obtained are not falsified by the movements of persons moving around the individual under surveillance, and so that the latter is not subjected to an excessive level of radiated energy. In addition, the consequences of prolonged exposure to microwave radiation are poorly understood, in particular as regards babies.

There is also known, i.e., from U.S. Pat. No. 4,350,166, a method wherein the modulation of the ambient infrared radiations by the carbon dioxide content of the exhalation of an individual is sensed. Thus, the sensors provide modulated signals and, if an interruption in the periodicity of these signal occurs, an alarm is triggered. However, there is always a risk that the ambient atmosphere surrounding the individual is disturbed by extraneous phenomena and that the detection is altered.

The invention aims to provide a method and an apparatus for monitoring the respiration of an individual, which method and apparatus make it possible to overcome the disadvantages of the prior art.

Since the risk factors involved in the respiratory events mentioned above are not known, only monitoring of the infants on a very large scale after their birth would ensure effective prevention. There is thus a need for a means for permitting the respiration of young infants to be monitored both in the hospital environment and at home, for detecting a respiratory insufficiency, apnoea or dyspnoea early, and for triggering an alarm in response to such a detection. Such a means must be adaptable to all sleeping arrangements, not require adjustment, and be easy to use and inexpensive.

SUMMARY OF THE INVENTION

To this end, the invention relates to a method for monitoring the respiration of an individual, in accordance with which the body of the individual is subjected at least partially to a field, the disturbances caused to the field by the movements of the individual are detected and an alarm is triggered when the degree of movement disturbing the field falls below a predetermined threshold for a period of time greater than a predetermined value, the method being characterized of that it consists of exposing the body of the individual at least partially to a luminous flux, forming on a set of photosensitive elements the image of at least one zone of the space exposed to the luminous flux and in the observation field of an optical means associated with the photosensitive elements, the zone including at least one part of the body of the individual liable to exhibit quasi-periodic movements associated with breathing, measuring and recording the gray levels of the points of the image constituted by the photosensitive elements subjected to the luminous flux transmitted back by the zone, repeating the measure and the record at a predetermined recurrence or reading frequency for recording successive images of the zone, comparing the gray levels of the corresponding points of successive images, and detecting a respiratory insufficiency, apnoea or dyspnoea, of the individual in the absence of significant variations or in the presence of abnormal variations in the spatial distribution of the gray levels of the points brightness of successive images compared.

The method according to the invention consists in observing the individual under surveillance of the presence of a luminous flux. This flux may consist of the existing light or may be produced by a luminous source which may have a very broad spectrum of the visible or non-visible range and which is not necessarily directive, since only the field of observations is important.

The method for monitoring according to the invention is periodic and sequential (and not continuous as in French Patent No. 147,047): the luminous image of one part of the body of the individual is received on a set of photosensitive elements and is read at regular time intervals by recording the gray levels of the points of this image.

A series of successive recorded images is thus obtained, and the spatial distribution of the gray levels is compared in pairs: if this spatial distribution is the same, it means that the individual is immobile and is no longer breathing. This characteristic of comparing the spatial distribution of the gray levels of images taken in pairs is completely unknown from French Patent No. 2,147,047.

It is important to note that with the method according the the invention it is possible to overcome variations in intensity of the luminous flux illuminating the individual: these variations affect the absolute values, but not the relative values and, therefore, the spatial distribution of the gray levels. These variations can therefore be ignored a priori, but they could also be measured in order to effect technologically the necessary corrections for the mean gray level. In both cases it is thus possible to "passively" detect an absence of movement of the individual, despite modifications occurring in the lighting conditions of the scene between two images compared.

According to one characteristic of the invention, the method consists in forming on the noted set of photosensitive elements a composite image which is the superposition of the images of several determined observation zones of a determined space in which the individual is liable to move, and in comparing the composite images.

According to another characteristic, the zones are distributed in the space in such a way that, in any position of the individual within this space, a part of his or her body liable to show movements associated with breathing is situated in at least one of the zones.

The space in question may be the bed in which an infant is lying. By choosing a judicious distribution of the observed zones and by superposing the images of these different zones on the set of photosensitive elements, the field of observation and the cost of the monitoring apparatus are limited, while ensuring that apnoea or dyspnoea can be detected whatever the position of the infant in its bed.

That part of the individual of which an image is formed will preferably be under substantially constant illumination in order to avoid gray level variations which would be due to changes in the lighting conditions.

The invention also relates to a device for monitoring the respiration of an individual liable to move within a determined space, characterized in that it comprises a lens forming an image of at least one zone of this space on a set of photosensitive elements, circuits for controlling and reading the photosensitive elements, an analog to digital converter, information-processing means, such as a microprocessor, in order to compare the signals successively supplied by the photosensitive elements and to determine the significant or abnormal variations in these signals which are due to the breathing of the individual, and alarm means triggered by the information-processing means in response to the detection of an absence of significant variations or the presence of abnormal variations.

According to a preferred embodiment, the device comprises optical means, such as prisms, forming on the set of photosensitive elements the composite image which is the superposition of the images of several determined zones of the space.

According to yet another characteristic, the device comprises a luminous source of infrared radiation of the non-visible range. When the room in which the infant is sleeping is made dark, this solution ensures substantially constant illumination of the observation field of the device, without disturbing the infant's sleep.

It should be noted that it was already known, from an article in MEDICAL AND BIOLOGICAL ENGINEERING AND COMPUTING (vol. 24, no. 2, March 1986, pages 193–196, IFMBE, Stevenage, Herts, GB; H. TEICHTAHL et al.: "Measurement of in vitro ciliary beat frequency: a television-video modification of the transmitted light technique"), to measure the ciliary cell beat frequency using a video camera, a microscope and a video system, observing the movements of the ciliary cells on the enlarged image present on the video screen.

However, this is a laboratory technique requiring the use of a high-power microscope since, according to an example given in the article, the cells observed are 0.2 $\mu$m wide and 6 $\mu$m long.

It was not obvious to a specialist in medical monitoring apparatuses to combine such different teachings as those in the article by TEICHTAHL et al. and in French Pat. No. 141,047 in order to arrive at the present invention; and in any case this combination does not suggest comparing the spatial distribution of the gray levels of successive images of the part of the body of the individual under surveillance.

Other characteristics and advantages of the invention will emerge from the following description of an embodiment given solely by way of example and illustrated by the attached drawings.

BRIEF DESCRIPTION OF THE DRAWINGS

FIG. 1 shows diagrammatically the installation of the device according to the invention on a cot.

FIG. 2 is a diagram showing the main components of the device according to the invention.

FIG. 3 is a diagrammatic side view showing the distribution of the observation zones of the device in FIG. 1.

FIGS. 4A and 4B show diagrammatically the time course of the main steps of the method according to the invention.

DETAILED DESCRIPTION OF THE PREFERRED EMBODIMENT

Reference will be made first to FIG. 1 in which the device 10 according to the invention is arranged, for example by means of a set of legs 11, above the bed 12 in which the infant 13 to be monitored is lying. It goes without saying that, if the nature of the bed permits, this device 10 may possibly be arranged on the side of the latter. Associated with the actual device 10 are a local light or sound alarm device 14 and a remote warning device 15 positioned at another site. The connection between the device 10 and the remote warning device 15 can be provided by any suitable means, for example by interphone or by a specialized or non-specialized information transmission channel (for example via an electrical network).

The main components of the device 10 will now be described with reference to FIG. 2. The device 10 comprises a lens 16, such as a camera lens, in the observation field of which is situated the bed 12 on which the infant 13 is lying.

The lens 16 is associated with a set of photosensitive elements consisting preferably of a bar or row 17 of elementary photodetectors 19, such as chargetransfer photodetectors, of which there may be 512 or 1024 for example.

The lens 16 forms on the bar 17 of photodetectors the image of a plane of the space included in its observation field, this plane corresponding to the plane of the drawing in FIG. 2. The positions of the lens 16 and of the bar 17 with respect to one another and with respect to the bed 12 are chosen in such a way that the plane of the observed space intercepts the plane defined by the surface of the mattress of the bed 12 in a zone of the latter in which is situated a part of the body of the infant 13 liable to exhibit movements associated with breathing, namely the thorax or abdomen.

However, since the infant is liable to move in its bed during sleep, it is preferable to form images of several different zones of the bed 12 which are distributed in such a way that, in any position of the infant in its bed, an image of a part of its thorax or its abdomen is formed on the bar 17. Thus, in accordance with the embodiment in FIG. 3, complementary optical means, such as prisms 18, are associated with the lens 16 in order to form images along three planes P1, P2 and P3 extending transversely with respect to the length of the bed 12. The optics 16, 18 are provided in such a way that the images of three bands Z1, Z2 and Z3 are superposed and give rise to a composite image on the bar 17 of photodetectors.

Of course, this is a particular exemplary embodiment which can be the object of many variants, both as regards the number of planes of the space observed and the orientations of these planes relative to one another and relative to the plane P of the mattress on which the infant is lying. These various parameters can be optimized as a function of the size of the bed 12, that of the infant, etc., in order to ensure that, in any position of the latter in its bed, at least one image of a part of its thorax or abdomen is formed on the bar 17 of photodetectors. However, there is no reason to multiply to excess the number of superposed images on the bar 17, since the result of this would be the risk of an excessive decrease in the sensitivity of the device by super-position of significant images (parts of the body of the child showing movements associated with breathing) and non-significant images (observation of zones of the bed in which there is no part of the body of the infant, or parts of the latter which do not show movements associated with breathing). In fact, each photodetector of the bar 17 is sensitive to the mean of the homologous points of the superposed images formed in the different planes of observation.

The photodetectors 19 of the bar 17 are associated with circuits, generally designated by reference number 20, which comprise circuits for measuring or reading the charges of the detectors 19, and at least one clock for determining the integration time or the reading frequency of the photodetectors 19. The reading circuits are connected via an analog to digital converter 21 to a microprocessor 22 effecting the processing of the output signals from the photodetectors 19 and the control of the circuits 20.

This microprocessor 22 also controls, by means of the circuits 20, a lighting system 23 which provides a substantially constant illumination of the bands Z1, Z2 and Z3, the images of which are formed on the bar 17. The lighting system 23 preferably consists of a set of photoemission diodes illuminating the abovementioned zones at a wavelength which is not within the visible range, but remains in the range of sensitivity of the photodetectors 19. Illumination by non-visible infrared has the advantage of not harming the infant at the intensities demanded by the sensitivity of the photodetectors, and of having a satisfactory degree of reflection on the numerous types of materials with which the infant 13 may be covered. If the lighting system is fed by an alternating voltage source, the reading frequency of the photodetectors must be equal to or be an integral sub-multiple of twice the frequency of the voltage source, so that the gray level of the photodetectors is independent of the source phase. By way of example, a reading frequency of 20 Hz is compatible with voltage sources of 50 Hz and 60 Hz.

The lighting system or luminous source 23 can be arranged in the immediate vicinity of the bar 17 of photodetectors, or else be at a slight distance from the latter in such a way as to illuminate obliquely the different zones observed Z1, Z2 and Z3 in order to contribute, by the formation of shadows in the region of these zones, to increasing the differences in brightness between the images of one and the same zone which are formed during a respiration cycle of the infant. It should be noted at this point that the infant will preferably not be covered by a blanket or clothing which is likely to render imperceptible those movements of its body which are associated with breathing. The infant may be clothed, for example, in a close-fitting garment. On the other hand, in the absence of a specific lighting system, the luminous source may consist of the natural light. In this case, means for controlling sensitivity can be provided, so that the mean gray level seen by the photodetectors is substantially constant and independent of the lighting conditions.

Furthermore, the microprocessor 22 is connected to the light or sound alarm device 14 associated with the device, and also to the remote warning system 15. These local alarm or remote warning means are triggered by the microprocessor 22 when it no longer detects breathing.

The main steps in the method according to the invention and the functioning of the device will now be described with reference to FIGS. 4A and 4B.

The curves a and b in FIGS. 4A and 4B represent the video signals obtained by reading of the elementary photodetectors 19 of the bar 17 at two instants which are separated by a predetermined time interval.

Each curve a, b represents the gray levels (brightness) which are viewed by the set of photodetectors 19. When the scene observed has not changed between the two observation instants, the curves a and b are identical (FIG. 4B), it being assumed that the lighting is substantially constant. In contrast, when there is a respiratory movement, this is reflected by a variation in the spatial distribution of the gray levels viewed by the corresponding photodetectors (FIG. 4A). The detection of the variations in the spatial distribution of the gray levels viewed by the photodetectors thus makes it possible to demonstrate those movements of the body associated with breathing and, consequently, the absence of these movements or an abnormal character thereof results in triggering of the warning system.

The processing of the video signals supplied by the bar 17 of photodetectors 19 is, in the main, as follows:

Two successive signals, such as those represented by the curves a and b, are compared, and their difference provides the signal represented by curve c. This signal is amplified (curve d) and is then straightened and converted into binary signals by comparison with a determined threshold permitting elimination of the residual noise of the photodetectors 19. The resulting signal, represented by curve e, comprises a first notch or echo 24, of a relatively considerable width (FIG. 4A), and a second notch or echo 25 of far lesser width. This signal is then applied to a filter in order to retain only the first echo 24 (curve f) which corresponds to a movement associated with breathing, and in order to eliminate the second echo 25 whose length is far too small to correspond to such a movement (case of an insect moving within the observation field).

In greater detail, the time course of the various operations in the method according to the invention may be as follows:

The images formed on the bar 17 of photodetectors are read at a determined frequency and the electrical charges of the set of photodetectors 19 scanned successively produce the video signals a and b in FIGS. 4A and 4B. These signals read by the circuit 20 and digitalized by the converter 21 are recorded by the microprocessor 22 at a frequency which is at most equal to the reading frequency and which is most often a sub-multiple of this reading frequency.

Let us assume, for example, that this time interval is 3 seconds and that the recording frequency is such that a recording is obtained every 0.5 second. In other words, the first signal recorded at instant 0 is compared 3 seconds later to the signal which has just been recorded and their difference is established as described with reference to FIG. 4 (amplification, straightening, conversion into binary signals and filtering) to give the result signal which is recorded at instant t=3 seconds. The signal recorded at time t=0.5 second is compared to the signal recorded at time t=3.5 seconds, and so on.

When a result is negative (no breathing), the following step consists in accumulating the following results a predetermined number of times or for a predetermined period of time and in giving the alarm after a predetermined and consecutive number of negative results indicating that the apnoea does not correspond to any respiratory pause, but to a respiratory arrest. This cumulative number of static images corresponds to the duration of the acceptable respiratory pause which may either be determined empirically and stored in the microprocessor 22, or set by means of a manually operated selector 24 provided on the device 10 (FIG. 1).

It goes without saying that the embodiments described are only examples and that they could be modified, in particular by substitution of technical equivalents, without thereby departing from the scope of the invention.

We claim:

1. Method for monitoring the respiration of an individual, comprising the steps of exposing the body of said individual at least partially to a luminous flux, forming on a set of photosensitive elements the image of at least one zone of the space exposed to said luminous flux and comprised in the observation field of an optical means associated with said photosensitive elements, said zone including at least one part of the body of the said individual liable to exhibit quasiperiodic movements associated with breathing, measuring and recording the brightnesses of areas of said image sensed by said photosensitive elements subjected to the luminous flux transmitted back by said zone, repeating said measuring and said recording at a predetermined reading frequency for recording the brightnesses of corresponding areas of successive images of said zone, comparing the brightnesses of said corresponding areas of successive images, and detecting a respiratory insufficiency, apnoea or dyspnoea, of said individual in the absence of significant variations or in the presence of abnormal variations in the spatial distribution of the brightnesses of the areas of successive compared images.

2. Method comparing according to claim 1, comprising the steps of forming on said set of photosensitive elements a composite image which is the superposition of the images of several determined observation zones of a determined space in which said individual is liable to move, and comparing successive composite images.

3. Method according to claim 1, comprising the step of distributing said zones in said space in such a way that, in any position of the individual within this space, a part of his or her body liable to show movements associated with breathing is situated in at least one of said zones.

4. Method according to claim 1, comprising the steps of recording the brightnesses of corresponding areas of successive images at a frequency which is a sub-multiple of said reading frequency and comparing in pairs the spatial distributions of the recorded brightnesses of the areas of successive images separated one from the other by a determined number of images the brightness of which has been recorded.

5. Method according to claim 4, comprising the steps of forming an analog electrical signal representing the brightness of all said areas of each said successive images, comparing the electrical signals associated with said successive images, and detecting a respiratory insufficiency in the absence of a significant difference between the amplitudes of the compared signals.

6. Method according to claim 5, comprising the steps of establishing a difference between the compared electrical signals, amplifying, straightening and converting in numerical form, by comparison with a determined threshold, the signal difference obtained, and filtering said numerical signal in order to eliminate the signals which are too small a dimension to correspond to a respiratory movement.

7. Method according to claim 4, comprising the step of comparing a predetermined number of results of successive comparisons in order to eliminate erroneous results due, in particular, to pauses in the respiratory cycle of the individual.

8. Method according to claim 4, comprising the step of comparing the spatial distributions of brightnesses of several successive images during each respiratory cycle of the individual.

9. Method according to claim 1, comprising the step of providing substantially constant illumination of the part of the individual of which an image is sensed.

10. Method according to claim 9, comprising the step of providing said illumination by means of a luminous source supplied by an alternating voltage source, the reading frequency being equal to or being an integral sub-multiple of twice the frequency of the alternating voltage source.

11. Device for monitoring the respiration of an individual whose body is liable to exhibit quasi-periodic movements associated with breathing, said device comprising:
- means for exposing at least partially to a luminous flux a predetermined space within which said body is liable to move,
- a set of photosensitive elements,
- a lens means for forming on said set of photosensitive elements an image of at least one zone of said space exposed to said luminous flux,
- reading means for repeatedly scanning said photodetector elements and for producing signals representative of the brightnesses of consecutive areas of said image sensed by said photodetector elements,
- recording means for recording said signals representative of the spatial distribution of the brightness of said image over said areas,
- processing means for:
  - comparing successive recorded signals representative of the spatial distribution of the brightnesses of successive images, and
  - detecting a respiratory insufficiency responsive to one of a significant and abnormal variations in the compared signals representative of the spatial distribution of the brightnesses of successive images, and
- alarm means triggered by said processing means in response to the detection of one of said significant and abnormal variations.

12. Device according to claim 11, wherein said recording means comprises means for recording the signals supplied by said reading means at a frequency which is a sub-multiple of the scanning frequency of the photosensitive elements, and said comparing means comprises means for comparing in pairs successive recorded signals separated one from the other by a determined number of signals and for establishing their difference.

13. Device according to claim 12, including circuits for conversion into binary signals of the differences of the signals compared, and filter networks for eliminating non-significant differences.

14. Device according to claim 11, including means for comparing a determined number of successive results produced by said processing means and for eliminating erroneous results.

15. Device according to claim 11, including optical means for forming on said set of photosensitive elements a composite image which is the superposition of the images of several determined zones of said space.

16. Device according to claim 15, wherein said optical means comprise prisms.

17. Device according to claim 11, including a luminous source of infrared radiation.

18. Device according to claim 11, wherein said recording means and said processing means are implemented in a microprocessor.

* * * * *